United States Patent
Eisen et al.

(12)

(10) Patent No.: US 6,284,482 B1
(45) Date of Patent: *Sep. 4, 2001

(54) METHOD FOR DETECTION OF ABNORMAL KERATINIZATION IN EPITHELIAL TISSUE

(75) Inventors: Drore Eisen, Cincinnati, OH (US); Stephen Frist; Joel Recht, both of Monsey, NY (US)

(73) Assignee: Oralscan Laboratories, Inc., Suffern, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,218

(22) Filed: Apr. 23, 1999

(51) Int. Cl.⁷ ...................................................... G01N 1/30
(52) U.S. Cl. ...................................... 435/40.52; 382/133
(58) Field of Search ............................... 435/40.5, 40.52; 382/133

(56) References Cited

U.S. PATENT DOCUMENTS 5,257,182 * 10/1993 Luck et al. ........................ 364/413.1
5,740,270 * 4/1998 Rutenberg et al. .................. 382/133

OTHER PUBLICATIONS

Schultz C. In Situ Infrared Histopathlolgy of Keratinization in Human Oral/Oropharyngeal Squamous Cell Carcinoma. Onocology Research 10(5)277–286, May 1998.*

* cited by examiner

Primary Examiner—Ralph Gitomer
(74) Attorney, Agent, or Firm—Levisohn, Lerner, Berger & Langsam (57) ABSTRACT

A sample of an epithelial lesion which may be keratinized is disclosed in which an analytical system including an imaging system is provided to detect precancerous and cancerous cells. A transepithelial non-lacerational brush produces sufficient cells from all three layers of the epithelium so that an analytical system comprising a programmed computer can detect which cells exhibit abnormal keratinization and require further examination because of a likely suspicion of said pre-cancerous and cancerous conditions. The method and system can apply to the diagnosis non-cancerous conditions as well.

26 Claims, 5 Drawing Sheets

METHOD FOR DETECTION OF ABNORMAL KERATINIZATION IN EPITHELIAL TISSUE

RELATED PATENT APPLICATIONS

This application is related to a prior application entitled "Minimally Invasive Apparatus and Method for Testing Lesions of the Oral Cavity and Similar Epithelium" filed on Apr. 23, 1999 and having Ser. No. 09/298,219.

FIELD OF THE INVENTION

The present invention is directed to determining whether or not there is a likelihood of detection of precancerous or cancerous conditions in epithelial tissue.

While this invention is described for testing lesions of the oral cavity, the methodology related to testing for abnormal keratinization applies to the analysis of any tissue sample in which keratin exists obtained by any medical technique.

BACKGROUND OF THE INVENTION

Detecting precancerous or cancerous conditions in certain body tissue is important. There are various methodologies of obtaining tissue samples for examination and methodologies for analyzing cellular specimens of the tissue samples.

One area of such activity is in the dental field. Between 5% to 10% of patients in general dental and medical practice have harmless appearing oral lesions which are routinely noticed on oral examination, or which are incidentally observed while performing a cosmetic or other dental procedure. Visual inspection and palpation of these lesions to detect early stage oral cancer is highly unreliable. This is because benign, dysplastic and cancerous lesions are often indistinguishable from each other on clinical inspection. The vast majority of these relatively benign appearing lesions are, in fact, benign. However, at least 6% of these benign appearing lesions may be pre-cancerous or cancerous, and failure to identify these dangerous lesions at an early, treatable stage, is a primary factor in the currently low five-year survival rate for oral cancer.

The dentist or physician who visually detects an oral lesion which is not clearly suggestive of precancer or cancer is faced with a quandary when restricted to the methods and apparatus of the prior art. The only accurate tool currently believed to be available in the prior art to distinguish benign from pre-cancerous and cancerous oral lesions is a lacerational or scalpel biopsy of the lesion followed by histological examination of the excised tissue. In a scalpel biopsy, a variety of surgical cutting instruments are used to obtain a tissue sample. If such a scalpel biopsy removes a part of the lesion it is referred to as an "incisional" biopsy, while if it removes the entire lesion it is referred to as an "excisional" biopsy.

In either case, a scalpel biopsy is a painful, lacerational, highly invasive procedure. Typical instruments for this purpose include, but are not limited to a flat scalpel blade, a round scalpel blade (punch biopsy) and scissors. Local anesthesia is always required. Considerable bleeding from the wound is common and suturing is often necessary. For these reasons, primary care dentists and physicians, those clinicians who most often encounter benign appearing oral lesions, are reluctant to perform a scalpel biopsy. When necessary, these clinicians will therefore generally refer the patient to an oral surgeon or oral pathologist for the procedure. Since as many as 5% to 10% of all patients in a typical dental or general adult medical practice may have such visible oral lesions, many of which are likely to be benign, performing a scalpel oral biopsy in the primary care setting or referral to a specialist for such performance is reserved for only the most clinically suggestive lesions. Yet, as has repeatedly been shown, pre-cancerous and cancerous oral lesions often mimic benign lesions. Lacking the subject invention, these pre-cancerous or cancerous, but benign appearing, oral lesions typically do not receive any immediate diagnostic evaluation and are thus allowed to progress to an advanced stage of oral cancer. Once such progression is underway and continues untreated, the patient's chances for recovery diminishes.

A prior art approach which has attempted to address this problem in testing lesions of the oral cavity was the use of cytology. In this approach, a sample of cells which was naturally exfoliated from the surface of a lesion into mucous or saliva is examined microscopically. While cytology is commonly used to detect precancer and cancer in other body sites, it has not proven to be useful in the oral cavity because of its low sensitivity, i.e. its high false negative rate. It is believed that this high false negative rate is in part due to the fact that many oral lesions have an overlying keratin layer which limits availability to the lesion surface of naturally exfoliated abnormal cells. In one large study, oral cytology was found to have a false negative rate of 30%. This means that 30% of oral lesions determined to, in fact, be precancerous or cancerous on scalpel biopsy and histology were falsely reported as "negative" using oral cytology. Due to its unreliable sensitivity, prior art cytologic technique is rarely used to test oral lesions or similar keratinized epithelial lesions for precancer or cancer.

SUMMARY OF THE INVENTION

In accordance with the invention, a unique processing system to analyze cellular specimens for abnormal keratinization is described. A cytological or cellular sample of an oral lesion is taken from a patient for analysis. In one embodiment, this sample is obtained by means of a non-scalpel instrument which is sufficiently abrasive to penetrate all three layers (basal, intermediate, and superficial) of the oral epithelium. In the preferred embodiment, this trans-epithelial sample is obtained by means of pressing and rotating a circular stiff nylon brush several times over the entire lesion surface. Alternatively, the sample can be obtained using cytology or histology, and can be any cellular specimen, including cells sloughed off naturally, or cells removed by a health care professional, including a tissue specimen or oral biopsy.

As an important feature of the subject invention, a cellular sample (preferably trans-epithelial) is examined with the aid of an image recognition system designed to identify minimal evidence of pre-cancerous and cancerous change. In accordance with the invention, the system can detect small numbers of abnormal cells distributed among the large number of normal cells obtained during the sampling procedure.

In this alternate or additional embodiment, the subject invention preferably overcomes the limitations and difficulties associated with analysis of cellular specimens for abnormal characteristics by providing an image recognition system which detects characteristics relating to abnormal keratinization of the cells. Preferably, these characteristics include color saturation associated with such abnormal keratinization.

In the preferred embodiment illustrating the invention, the system described overcomes the sensitivity limitations of prior art oral cytologic technique by combining innovations in oral pathology, namely: 1) a non-scalpel cellular sample of all three layers of the oral epithelium; and 2) subjecting this novel sample to inspection by the novel image recognition system specifically designed to detect minimal evidence of early precancerous change in a trans-epithelial sample from an oral lesion, or other lesion with similar epithelia. This novel image recognition system which is the subject of this patent application preferably analyzes for the presence of abnormal keratinization, by detecting predetermined characteristics of color saturation.

For purposes of this patent application, the prior art scalpel procedure is defined as lacerational, whereas the sample collection device herein is non-lacerational and therefore minimally invasive. To the extent that an abrasive brush has characteristics that may cause minor discomfort and/or bleeding, there is substantial difference between the prior art scalpel trauma and the minimal trauma associated with the present invention.

Thus, in the preferred embodiment of the invention, the image processing system combines: 1) sensitivity to the presence of abnormal cellular morphology obtained from any or all of the three layers of the novel trans-epithelial cellular sample with 2) sensitivity to the presence of abnormally keratinized cells as are commonly found in any or all of the three layers of the epithelia and also obtained by means of the novel trans-epithelial cellular sample of the subject invention. Thus, the keratin component, which presented an obstacle to prior art oral cytology, is both penetrated, to ensure that any underlying abnormal basal cell morphology is available for analysis, and productively utilized, as a means of increasing the method's overall sensitivity to evidence of precancerous and cancerous change.

In a preferred embodiment, the image recognition system selects the most suspect abnormal cells and cell clusters among the sample, and displays these cells and cell clusters on a video monitor for expert review.

In the preferred embodiment, the image recognition system also provides a color printout of those suspect cells and cell clusters selected by the expert reviewer as representative of the case.

In the preferred embodiment, the image recognition system selects abnormal cells based on morphological characteristics and on overall resemblance to abnormal cells on which it has been trained.

In the preferred embodiment of the invention, the image recognition system is directed to detection of abnormality of the oral cavity by including a function to detect abnormal keratin as is often found in dysplastic and cancerous oral tissue.

In the preferred embodiment of the invention, the image recognition system is directed to detection of abnormal keratin by being programmed to detect a threshold level of color saturation associated with "hyalinization" or the stained appearance of such abnormal keratin.

In a further preferred embodiment of the invention, the image recognition is directed to the combination of morphological cellular change associated with pre-cancer and cancer and the appearance of abnormal keratin as produced by pre-cancerous and cancerous cells of the oral cavity and similar epithelia.

In one embodiment of the invention, the image recognition system may be constructed through modification of image recognition systems currently manufactured and sold to detect abnormal cells spontaneously exfoliated from non-keratinized lesions such as cervical lesions.

ADVANTAGES OF THE INVENTION OVER THE PRIOR ART

The invention describes a method and system which provides accurate evaluation of oral lesions.

In a multi-center clinical trial with over 800 patients performed at 35 U.S. Academic Dental Centers, the sensitivity and specificity of the subject invention was compared to the prior art technique of scalpel biopsy and histology. In this double blind study, the subject invention was found to detect 100% of the pre-cancerous and cancerous lesions detected by the prior art technique. The subject invention thus had a 0% false negative rate in this study. As noted above, this contrasts with false negative rates as high as 30% commonly associated with prior art oral cytology. In addition, the subject invention had less than a 1% false positive rate in this study. In this study, the subject invention also detected pre-cancer or cancer in approximately 15 patients whose lesions did not visually appear suspicious enough to expert examiners to warrant a scalpel biopsy. These outcomes represent lives that were potentially saved by the subject invention.

An additional advantage of the subject invention over the prior art diagnostic technique is greater sensitivity to the detection of pre-cancer and cancer in large multi-focal oral lesions. This is because of the larger sampling area obtained by the brush biopsy technique of the subject invention when compared to the smaller area sampled by a traditional incisional scalpel biopsy.

An additional advantage of the subject invention is that patients which have chronic oral lesions can have these lesions followed over time by repeated testing using a minimally invasive procedure.

An additional advantage of the subject invention is that it allows accurate, minimally invasive testing of lesions from areas of the body outside of the oral cavity where a keratin layer that limits the accuracy of prior art cytological technique may be present. Several such areas are the larynx, pharynx, esophagus, and vulva.

An additional advantage of the subject invention is that it allows diagnosis of non-cancerous conditions, such as candidiasis, herpes, geographic tongue, lichenplanus, human papilloma virus, and others.

DETAILED DESCRIPTION OF THE INVENTION AND THE PREFERRED EMBODIMENTS

It is known that the functional differentiation of euplastic tissues to form keratinized stratified squamous epithelium is characterized by certain important morphological features.

Frost, for example, discusses this differentiation, and the prototypical morphology at length. See, John K. Frost, The Cell in Health and Disease: An Evaluation of Cellular Morphologic Expression of Biologic Behavior, $2^{nd}$ edition, Chapter 11, in Monographs in Clinical Cytology, vol. 2 (New York: Karger 1986). Specifically, such cells display a central nucleus, a thread-like chromatin pattern, karyopyknosis with maturation, intercellular bridges, stratification, keratinization, thinning, orientation parallel to the basement membrane and lumen, and exfoliation as single cells.

In accordance with the present invention, an automated, computer implemented, system is provided for detection of such differentiation, particularly for cells of the oral cavity and similar epithelium. As such, the invention provides a means for alerting physicians to the presence of cancerous or pre-cancerous cells at an early stage by overcoming the disadvantages of the prior art which has tended to avoid early detection.

Accordingly, in one embodiment of the present invention, a sample of cells from the oral cavity or similar epithelia is processed by an image analysis system for detection of characteristics associated with dysplasia or cancer. In one embodiment of the invention, the sample is a standard sample of cells, taken as known in the prior art. In an alternate embodiment, the sample is a sample taken using a nonlacerational sampling device. In either embodiment, the sample can be sent to an automated image processing system for detection of abnormal keratinization.

In accordance with the preferred embodiment of the invention, it is important that a transepithelial sample be taken from the oral cavity or similar epithelia, the sample being obtained using a nonlacerational sampling device. This cytological or cellular sample of the entire epithelial thickness of an oral lesion is preferably obtained using a non-scalpel instrument which is sufficiently abrasive to penetrate all three layers (basal, intermediate, and superficial) of the oral epithelium. In the preferred embodiment, the device is the sampling instrument disclosed in U.S. Provisional Patent Application Ser. No. 60/093,910, filed Jul. 23, 1998 and entitled "Apparatus and Method for Performing a Non-Lacerating Biopsy of Lesions of the Oral Cavity and of Similar Epithelium",the disclosure of which is fully incorporated herein by reference, or is the Spirabrush™, available from The Trylon Corporation of Torrance, Calif., or the like. In the preferred embodiment, this trans-epithelial sample is obtained by means of pressing and rotating a circular stiff nylon brush several times over the entire lesion surface. This sample is then analyzed by an automated image processing system for detection of morphology or characteristics typical of dysplasia or cancer.

In the preferred embodiment of the invention, the transepithelial sample is analyzed by an image processing system for detection of the presence of abnormal keratinization. In a further preferred embodiment, the sample is also analyzed for the presence of other characteristics or morphology associated with dysplasia or cancer. If desired, this analysis can be done with any cellular sample, whether a sample obtained by histology or cytology, and can include cells naturally sloughed off, cells intentionally rubbed off, or a tissue sample from an oral biopsy. Although such techniques can be used in conjunction with the invention, however, they do not constitute the preferred embodiment, as it is preferred that a brush biopsy be performed.

Figure 4:
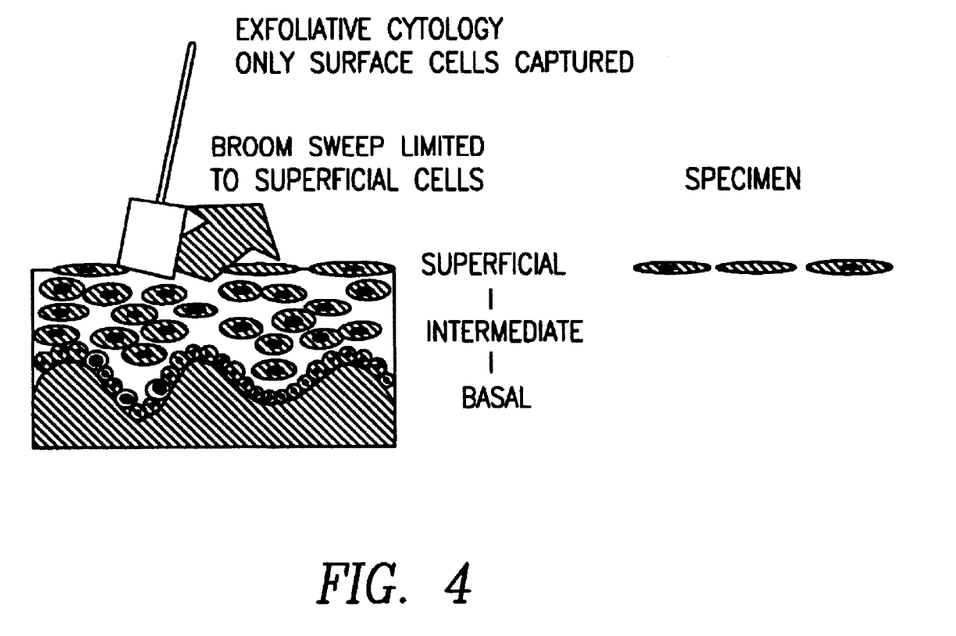
FIG. 4 is a cross sectional view of an section of epithelium including pre-cancerous or cancerous cells, showing the extent of sampling obtained using exfoliative cytology.
Figure 5:
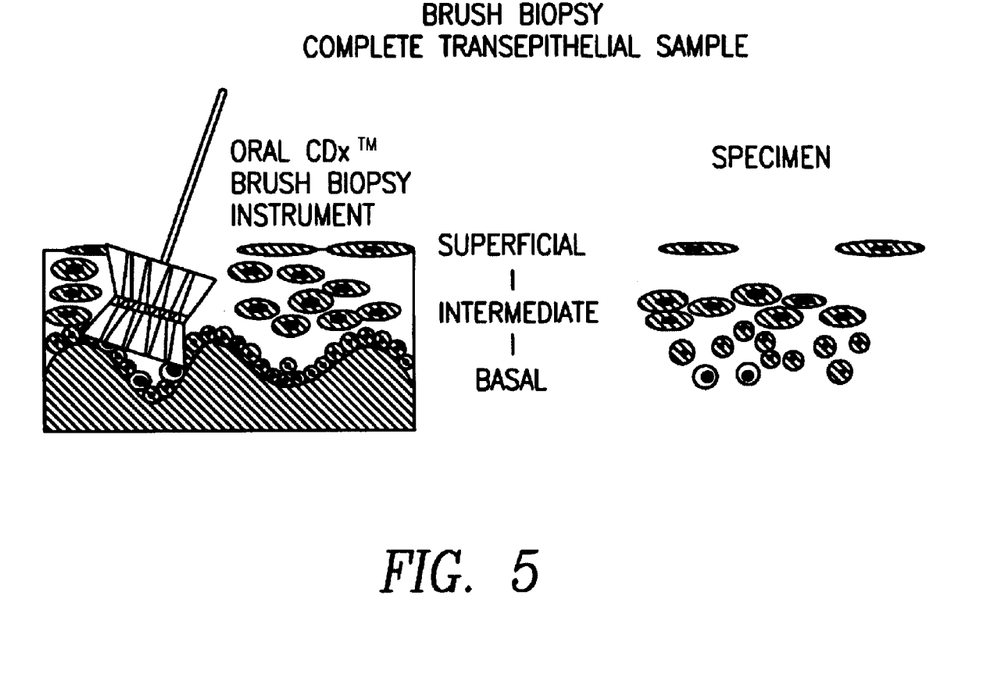
FIG. 5 is a cross sectional view of an section of epithelium including pre-cancerous or cancerous cells, showing the extent of sampling obtained using the brush biopsy technique of the present invention.

As shown in FIG. 4, in the prior art method of exfoliative cytology a non-abrasive sweep is conducted of the epithelial surface in a region of interest which typically only captures surface and exfoliated cells from the epithelial area. Abnormal cells 37 located below the surface, for example, cells located at the basal layer, will therefore often be missed using this superficial sampling. As a result, the specimen sent for analysis, will lack these deeper cells, and may therefore result in a false negative diagnosis. In accordance with the preferred embodiment of the present invention, in contrast, a brush biopsy is taken, using the brush biopsy instrument disclosed, the brush being used to penetrate below the surface of the epithelium and obtain cells from all three epithelial layers. Thus, the specimen sent for testing includes abnormal cells regardless of whether they are cells from the superficial layer or the deeper intermediate and basal layers, providing a more complete and accurate cellular sample for analysis.

In the preferred embodiment, the subject invention thus combines two innovations in oral pathology, namely, a cellular sample of all three layers of the oral epithelium obtained without the use of a scalpel or similar lacerational instrument, with an analysis of that sample by a novel image recognition system specifically designed to detect minimal evidence of early pre-cancerous change in that transepithelial sample from an oral lesion, or other lesion with similar epithelia. In the preferred embodiment of the invention, the image processing system combines sensitivity to the presence of abnormal cellular morphology obtained from any of the three layers of the epithelia with sensitivity to the presence of abnormally keratinized cells as are found in any of the layers of the epithelia. In contrast to the prior art, the keratin component, which previously presented an obstacle to prior art oral cytology, is penetrated to ensure that any underlying abnormal intermediate and basal cell morphology is available for analysis and productively utilized as a means of increasing the method's overall sensitivity to evidence of pre-cancerous and cancerous change.

In one preferred embodiment, the invention utilizes a modified version of the commercially available PAPNET system, currently sold by Neuromedical Systems, Inc. of Upper Saddle River, N.J. and Suffern, N.Y. Further details of such systems are described in U.S. Pat. No. 4,965,725, entitled "Neural Network Based Automated Cytological Specimen Classification System and Method"; U.S. Pat. No. 5,257,182, entitled "Morphological Classification System and Method"; U.S. Pat. No. 5,287,272, entitled "Automated Cytological Specimen Classification System and Method"; U.S. Pat. No. 5,232,207, entitled "Inspection Apparatus and Method with Inspection Auditing for Images Presented on a Display"; U.S. Pat. No. 5,544,650, entitled "Automated Specimen Classification System and Method"; U.S. Pat. No. 5,625,705, entitled "Intensity Texture Based Classification System and Method"; U.S. Pat. No. 5,629,766, entitled "Global MTF Measurement System"; U.S. Pat. No. 5,655,029, entitled "Device and Method for Facilitating Inspection of a Specimen"; U.S. Pat. No. 5,659,421, entitled "Slide Positioning and Holding Device"; and U.S. Pat. No. 5,740,270, entitled "Automated Cytological Specimen Classification System and Method",the disclosures of which are fully incorporated herein by reference. In alternative embodiments, the invention utilizes a modified computer image recognition system having similar or equivalent capability to detect and present abnormal cells within certain predetermined parameters.

Currently, oral lesions which are routinely noticed on oral examination, or are incidentally observed while performing a cosmetic or other dental procedure, are only rarely biopsied or tested to detect early stage cancer. In accordance with the present invention, however, the dentist or physician, or other expert who visually detects such lesions can routinely test them to detect abnormality with a minimum of discomfort to the patient.

In accordance with the invention, such testing is conducted to obtain a transepithelial sample of the lesion which can them be sent for staining and subsequent analysis by a computer implemented system. Accordingly, in the first step of the present invention, a transepithelial sample is taken from the patient's oral lesion.

In accordance with the preferred embodiment of the invention, the cytological or cellular sample is taken of the entire epithelial thickness of an oral lesion by means of a nonlacerational or nonscalpel instrument which is sufficiently abrasive to penetrate all three layers (basal, intermediate, and superficial) of the oral epithelium. Preferably, this trans-epithelial sample is obtained by means of pressing and rotating a circular stiff nylon brush several times over the entire lesion surface. In a preferred embodiment of the invention, the sample is taken using the brush disclosed in pending U.S. Provisional Patent Application Ser. No. 60/093,910, filed Jul. 23, 1998 and entitled "Apparatus and Method for Performing a Non-Lacerating Biopsy of Lesions of the Oral Cavity and of Similar Epithelium",the disclosure of which is fully incorporated herein by reference, or the Spirabrush™, available from The Trylon Corporation of Torrance, Calif.

Upon sampling of the lesion, the sample is stained preferably using the modified Papanicolaou stain, as is well known in the art. This stained sample is then imaged and analyzed using an image recognition system which selects abnormal cells based on a combination of abnormal morphology and abnormal keratinization particularly the characteristics associated with lesions of the oral cavity and similar epithelia.

In the preferred embodiment of the invention, the image recognition system first processes the image through an algorithmic classifier and then sends the processed data to a neural net work. The algorithmic classifier locates a first group of candidate objects within the image which could be the nuclei of cells. In accordance with the invention, the algorithmic classifier has been modified to also locate a second group of candidate objects within the image, these being cells displaying the abnormal keratinization typical of precancerous and cancerous lesions of the oral cavity. The neural net then scores cells for the presence of other morphological features associated with cancerous cells.

In one preferred embodiment of the invention, these two candidate groups are both sent to the neural net for scoring, and the highest ranking objects from the combined two groups are displayed to the expert reviewer. In an alternate embodiment of the invention, those cells displaying abnormal keratinization do not compete with other cells in the neural net stage of analysis; rather, all abnormally keratinized cells are forwarded for display to the expert reviewer.

In one preferred embodiment, the stained sample is analyzed by a modified PAPNET system, the system being modified as described herein. Such PAPNET systems are commercially available image recognition systems which select the most suspect abnormal cells and cell clusters among those presented in a stained sample, and then display these cells and cell clusters on a video monitor for expert review.

In the present state of such PAPNET systems, the programming of the system is set to detect and display the top 64 glandular cells or top 64 clusters of cells, and the top 64 squamous cells or top 64 single cells, the ratio of glandular to squamous cells or cell clusters to single cells being in a 1:1 ratio, these top cells being those cells ranked highest for abnormalities by the system.

In accordance with the present invention, the programming of the system is modified to vary this detection ratio to enhance the system's performance on oral brush biopsies of the oral mucosa. In accordance with the invention, the system is reprogrammed to detect and display the top 64 clusters of cells and the top 128 single cells, in a 1:2 ratio. Although a 1:2 ratio is used in the preferred embodiment, in other embodiments modifications can be made to the controller such that a 1:3 ratio, or some other ratio higher than 1:1 can be employed. Accordingly, by modification of this detection parameter the detection capabilities for abnormalities in oral lesions is improved.

In its current form, the commercially available PAPNET system is programmed to analyze the visual image of the stained sample to detect abnormalities consistent with the presence of a cancerous or precancerous condition. In accordance with the present invention, the current programming is still utilized and such abnormalities are located. However, in addition thereto, the system is reprogrammed such that a further set of parameters are introduced to enhance the system's detection capabilities, by isolating a second group of candidate cells. Specifically, in the preferred embodiment of the invention, the image recognition system is directed to enhance its detection of abnormalities of the oral cavity by including a function to detect abnormalities such as are characteristic of dysplastic and cancerous oral tissue. In the preferred embodiment, the system detects abnormal keratin. These keratinized cells are then either forwarded to the neural net for detection of abnormalities consistent with cancer or precancer, or are forwarded directly to an expert for analysis.

Another method to detect abnormal samples is to set threshold levels for morphology and/or color, which threshold levels indicate, if exceeded, that there is a likelihood of abnormal cells in the sample being analyzed.

Research has indicated that lesions of the oral cavity and similar epithelium often display a progressive keratinization. This process of keratinization occurs throughout the epithelial layers. These keratins typically occur uniformly throughout the cytoplasm. In accordance with the present invention, several morphologic features present in the routine Papanicolaou stain are used to facilitate the detection and identification of these keratins. The most distinctive characteristic of the presence of the more mature keratins is a hyalinization, or glassy appearance to the cytoplasm. As Frost has described, for example, this hyaline character often imparts to the cytoplasm "the impression of viewing a brilliantly gleaming colored glass of a stained glass window, with the sun beaming in from behind." Other observers have described the appearance as "shiny", "metallic" or "glowing." A second important characteristic associated with these keratins is the presence of a particular color. As the process of keratinization develops, samples obtained by staining change from basophilia (i.e. green to blue) toward acidophilia (e.g. yellow or orange to red). In accordance with the present invention, an orange to red color is looked for, or a deep 'Halloween orange'.

Accordingly, in the preferred embodiment of the invention, the PAPNET system is redesigned or reprogrammed to detect "glowing" or glassy, orange-red cytoplasms, as are associated with abnormal keratinization of oral and similar epithelia. In the preferred embodiment, the algorithmic classifier is programmed to take the cells of the stained sample and to further perform an analysis of their color. In one embodiment, each pixel of the image is separately screened or tested for distinctive color characteristics. In an alternative embodiment, the cells are first screened and detected for abnormality by the system using the standard parameters of the PAPNET system (with a modified detection ratio as described above) and are then analyzed for distinctive color.

In this color detection step of the preferred embodiment, every pixel of the image is preferably measured to detect the pixel's Hue (H), Intensity (I) and Saturation (S). The target Hue sought is an orange-red, such as that commonly associated with abnormally keratinized cytoplasm. In one preferred embodiment, the system searches for a Hue of approximately 46–82 on a scale ranging from 0–255. In addition to Hue, the target pixels which the system searches for are those cells which further have a high Intensity and a high Saturation. Specifically, in one preferred embodiment, the system is set to search for and detect pixels with an Intensity of 100–255 on a range of 0–255. Likewise, in the preferred embodiment, the system is set to detect a Saturation of 43–255, also on a range of 0–255.

Having been set with the desired parameters of H, I and S, in the preferred embodiment the system is programmed to analyze each pixel of the sample image and to narrow down the target pixels of interest to those pixels displaying all of the preferred parameters of desired Hue, Intensity and Saturation. RGB analysis could also be employed.

Once the pixels with the desired color characteristics have been isolated, a morphological closing, i.e. a dilation and an erosion, is mathematically performed by the system to find round objects. Such closings are known in the art, and are used, for example, elsewhere in the prior unmodified PAPNET system for purposes unrelated to the detection of abnormal keratin. Likewise, Pratt describes such closings and the mathematics of the same. See, William K. Pratt, Digital Image Processing, Second Edition, Chapter 15, Morphological Image Processing (New York: John Wiley & Sons).

In accordance with the present invention, the morphological closing operation on these pixels with the desired color characteristics is performed using a 9×9 (octagonal) structuring element. (The 14×14 structuring element used by the PAPNET system in a separate step unrelated to color processing can still be used, however, in that separate step of the image processing). The 9×9 structuring element used in this stage of the process tends to find round objects, and will find those which are approximately 2–18 microns in diameter.

Once this closing has been performed, a sizing is performed. In this step, objects under 10 microns in diameter are rejected from consideration. Such filtration of objects based on size is well known in the art, having been used in other applications, among them the unmodified PAPNET system, and is discussed, for example, in U.S. Pat. No. 5,257,182 issued to Luck et al., and entitled "Morphological Classification System and Method".

Once this sizing step has been conducted, the system has now effectively selected round objects with a glowing cytoplasm that meet the criteria of abnormally keratinized cells of the oral cavity. The system then cuts out a window of approximately 48 microns by 48 microns around the centroid of each such object, forming the second group of candidate objects.

In the preferred embodiment of the invention, the first group of candidate objects (those objects which have been isolated by the algorithmic classifier without reference to color characteristics) and the second group of candidate objects (those cells isolated based on color characteristics that indicate the presence of abnormal keratinization) are both sent to the neural net for scoring, and the highest ranking objects from the combined two groups are displayed to the expert reviewer.

Figure 1:
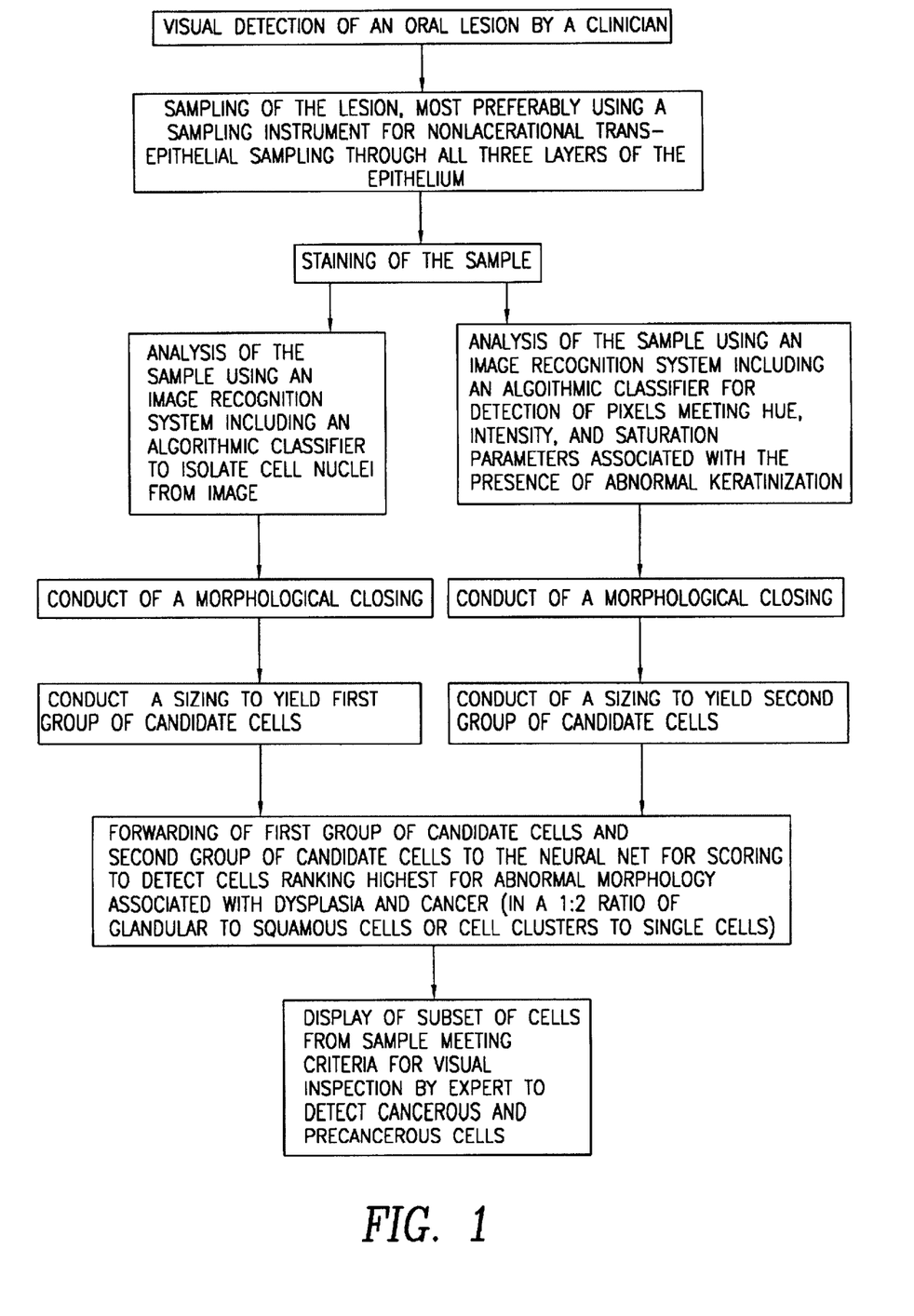
FIG. 1 is a flowchart illustrating the method of one embodiment of the present invention.
Figure 2:
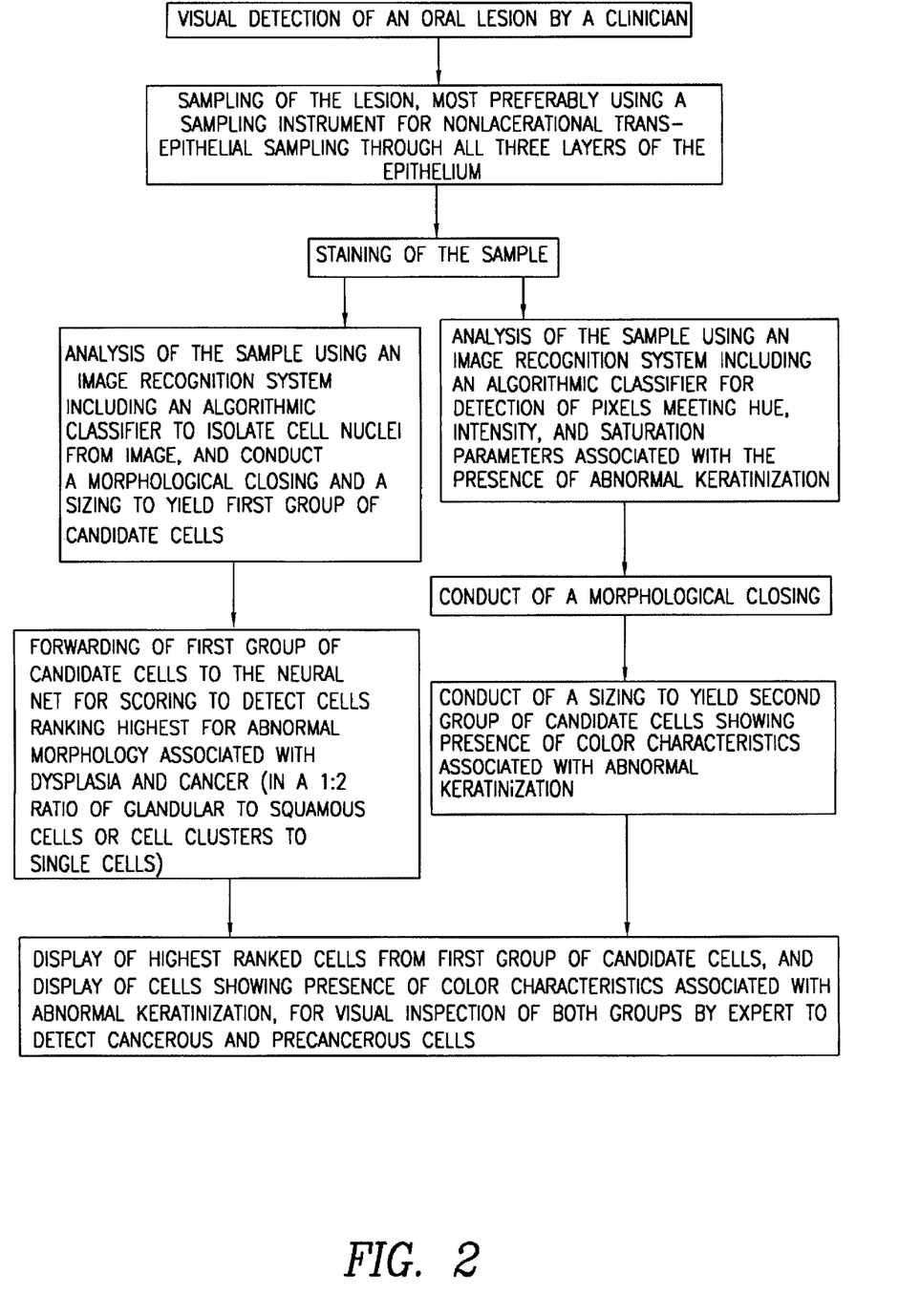
FIG. 2 is a flowchart illustrating the method of an alternate embodiment, in accordance with the present invention.

In an alternate embodiment of the invention, as shown in FIG. 2, those cells displaying abnormal keratinization do not compete with other cells in the neural net stage of analysis. Rather, the first group of candidate cells is scored by the neural net, and the second group of candidate cells bypasses the neural net and is directly forwarded for display to the expert reviewer.

Figure 3:
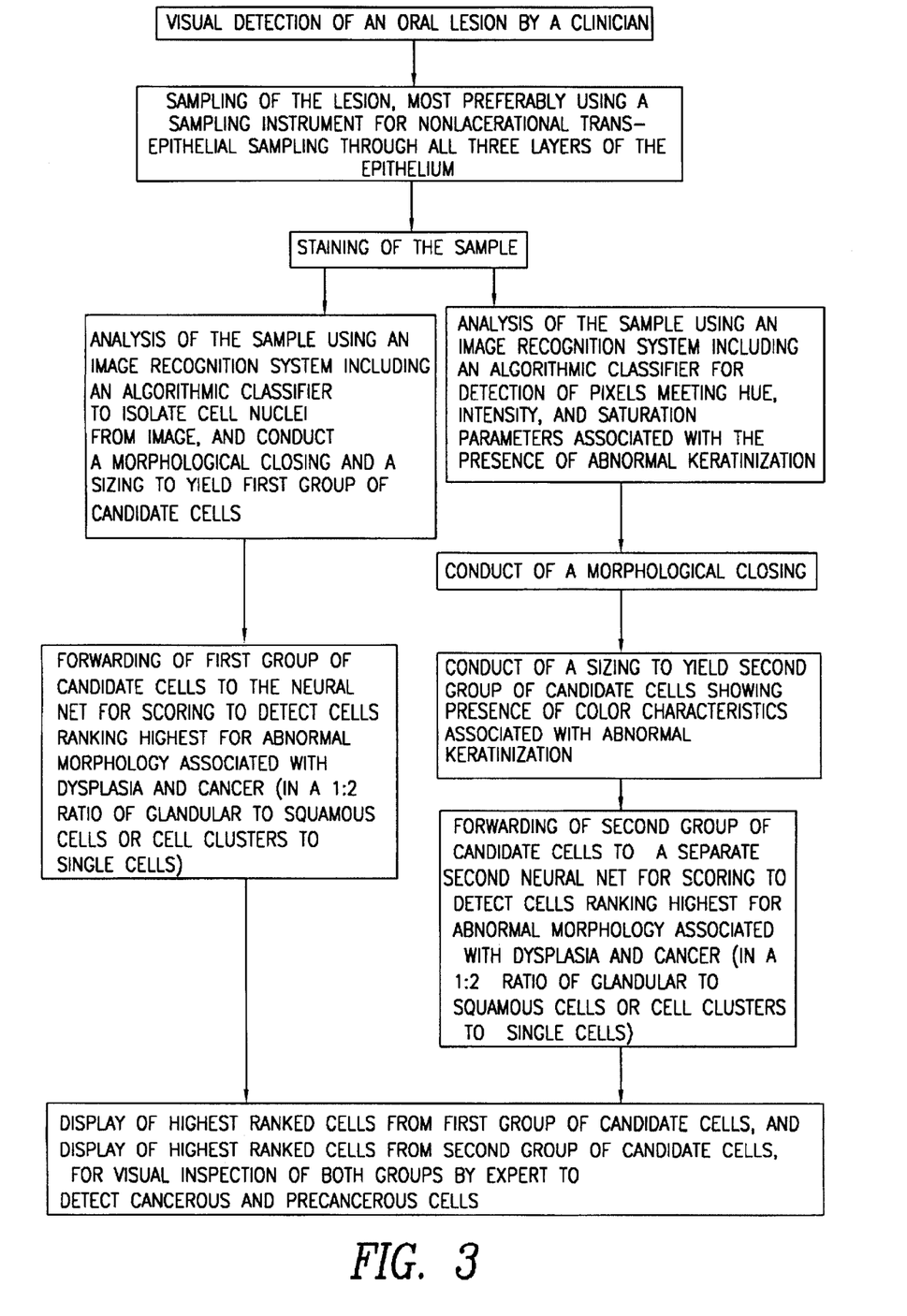
FIG. 3 is a flowchart illustrating the method of a third embodiment, in accordance with the present invention.

In yet a further alternate embodiment of the invention, as shown in FIG. 3, those cells displaying abnormal keratinization are sent to a separate, second neural net for independent ranking by a neural net, but also without having to compete with other cells in the neural net stage of analysis. Thus, the first group of candidate cells is scored by a first neural net, and the second group of candidate cells is scored by a second neural net, with each group of cells being forwarded for display to the expert reviewer.

A pathologist, cytologist or other expert reviewer can then visually examine the objects forwarded for the display, the objects being displayed on a video monitor. Upon visual inspection, the reviewer can then make a determination whether a cancerous or precancerous condition is present. Preferably, in accordance with the invention, the image recognition system also provides a color printout of those suspect cells and cell clusters selected by the expert reviewer as representative of the case.

An alternative embodiment to scoring and displaying the cells to an expert reviewer is to program the system to set certain threshold levels both for morphological abnormalities and/or abnormal keratinization. When those threshold levels are exceeded, the system will automatically produce a visualization of only such specific cells and not those highest scored or highest ranked on the specimen regardless of whether or not the scores have exceeded the threshold level.

In a further embodiment of the invention, the system can be programmed to detect and display basal cells using a basal cell detector in the algorithmic classifier. Alternatively, the pathologist can merely examine the cells in the sample with a standard microscope to detect the presence of basal cells. This embodiment provides a "fail-safe feature" within the overall testing process to ensure that a transepithelial sample has been obtained, i.e. that the cellular sample includes cells from all three layers of the epithelia. Should the pathologist determine that basal cells are not, in fact, present, the incomplete sample can be disregarded if negative and sampling can be repeated to attempt to obtain a transepithelial sample for analysis. In this manner, the pathologist will not rely on the incomplete sample for the test results. Thus, if the initial sampling fails to obtain a transepithelial sample, that deficiency is detected in advance and the patient will not obtain a false sense of security from a false negative.

The PAPNET system, as is commercially available was designed for a platform with a neural network which has relatively slow processing speeds. Because of the large number of cells in the original sample requiring examination, and the speed of the original PAPNET neural network, a multiple stage analysis was performed in which the population of cells to be analyzed by the neural network was necessarily reduced at each stage to allow the overall process to run in a reasonable time. For example, if 500,000 cells were in a sample, a first analytical stage applying algorithmic, first stage neural network or other analytical techniques could reduce that population to approximately 50,000 cells, which could then be realistically examined by the processing speed of the then available neural networks.

Due to the increased speed of microprocessors and computers, the decisional analysis to determine either threshold level crossings, color analysis or morphological analysis can be accomplished with a single stage neural network. A single stage neural network is meant to indicate that there may be different layers within the neural network, but the entirely of the process can occur in a single stage without prior elimination of objects requiring neural network analysis.

With current processors, such as a Pentium 300, a single neural network stage can be implemented in which the entirety of the population of sample cells can be analyzed in a sufficiently short period of time to realize practical operation.

Having described this invention with regard to specific embodiments, it is to be understood that the description is not meant as a limitation since further embodiments, modifications and variations may be apparent or may suggest themselves to those skilled in the art. It is intended that the present application cover all such embodiments, modifications and variations.

What is claimed is:

1. A method to detect abnormal cells in sample cells of epithelial tissue of the body, such sample cells having been collected by non-lacerational techniques collecting said sample cells from among the superficial, intermediate and basal layers of said epithelial tissue, wherein said method analyzes the sample cells, said method comprising:

using a computer to detect and display selected cells of said sample cells, analyzing the selected cells collected to detect abnormally keratinized cells, wherein said epithelial tissue is oral mucosa, said method includes the step of analyzing the sample cells to determine if cells have been collected from the basal layer, further including that if no abnormal cells are detected, the step of determining that if cells have not been collected from said basal layer that the detection of abnormal cells was incomplete and the analysis should be disregarded.

2. The method as set forth in claim 1, further comprising the step of imaging said abnormally keratinized cells.

3. The method as set forth in claim 2, further comprising the step of selecting the most suspect abnormal cells among the sample cells and imaging said suspect cells.

4. The method as set forth in claim 2, further comprising the steps of detecting which of said sample cells exhibit abnormal morphology and classifying said cells which exhibit abnormal morphology.

5. The method as set forth in claim 4, further comprising the step of conducting a morphological closing.

6. The method as set forth in claim 5, further comprising conducting a sizing to yield a first group of candidate cells.

7. The method as set forth in claim 6, further comprising the steps of conducting a morphological closing of cells associated with the presence of abnormal keratinization and conducting a sizing of said cells associated with the presence of abnormal keratinization to yield a second group of candidate cells.

8. A method to detect abnormal cells in epithelial tissue of the body according to claim 7, further comprising the step of analyzing the first group of candidate cells and said second group of candidate cells to rank those having the highest abnormal morphology and displaying a subset of said cells.

9. The method as set forth in claim 7, further comprising the step of displaying the highest ranked cells from the first group of candidate cells which show the presence of color characteristics associated with abnormal keratinization and visually inspecting the displayed cells.

10. The method as set forth in claim 6, further comprising producing a second group of candidate cells related to color saturation characteristics.

11. The method as set forth in claim 10, further comprising the step of imaging the first or second group of candidate cells.

12. The method as set forth in claim 10, further comprising the step of analyzing said first and second groups of candidate cells to rank those cells having the highest probability for being abnormal cells.

13. The method as set forth in claim 1, further comprising the step of detecting color properties associated with abnormal keratinization.

14. The method as set forth in claim 1, comprising the step of staining said cells to produce a stained appearance of abnormal keratin.

15. The method as set forth in claim 14 comprising the step of algorithmically classifying said stained cells, imaging said stained cells, isolating cell nuclei from said image, conducting a morphological closing and conducting a sizing to yield a first group of candidate cells.

16. The method as set forth in claim to claim 1, comprising the step of setting a threshold level relating to characteristics of the sample cells and detecting when the characteristics of said sample cells exceed said threshold level.

17. The method as set forth in claim 16, wherein the characteristics of the sample cells relate to the color characteristics thereof.

18. The method as set forth in claim 17, wherein the color characteristics relate to color saturation.

19. The method as set forth in claim 18, wherein the color characteristics relate to the appearance of abnormal keratinization.

20. The method as set forth in claim 18, wherein the characteristics of the sample cells relate to morphological characteristics.

21. The method as set forth in claim 16, wherein the characteristics of the sample cells relate to morphological characteristics.

22. The method as set forth in claim 1, wherein said sample cells are obtained by histological techniques.

23. The method as set forth in claim 1, wherein said sample cells are obtained by cytological techniques.

24. A method as set forth in claim 1, wherein said selected cells are in clusters.

25. A method as set forth in claim 1, wherein said selected cells are single cells as well as cells in clusters.

26. A method to detect abnormal cells in epithelial tissue body according to claim 1, wherein said selected cells are single cells.

* * * * *